United States Patent [19]

Tung et al.

[11] 4,182,818

[45] Jan. 8, 1980

[54] POLYFUNCTIONAL LITHIUM CONTAINING INITIATOR

[75] Inventors: Lu H. Tung; Grace Y-S. Lo, both of Midland, Mich.

[73] Assignee: The Dow Chemical Company, Midland, Mich.

[21] Appl. No.: 824,883

[22] Filed: Aug. 15, 1977

[51] Int. Cl.$^2$ .............................................. C08F 4/48
[52] U.S. Cl. .............................. 526/173; 260/665 R; 526/181
[58] Field of Search .............................. 526/173, 181; 260/665 R

[56] References Cited

U.S. PATENT DOCUMENTS

| | | | |
|---|---|---|---|
| 3,644,322 | 2/1972 | Farrar | 526/173 |
| 3,734,973 | 5/1973 | Farrar | 526/173 |
| 3,763,126 | 10/1973 | Farrar | 526/173 |
| 3,787,510 | 1/1974 | Farrar | 526/173 |
| 4,020,251 | 4/1977 | Hsieh | 526/173 |
| 4,067,917 | 1/1978 | Sigwalt et al. | 526/173 |

FOREIGN PATENT DOCUMENTS 4618721  11/1968  Japan ......................................... 526/173

Primary Examiner—William F. Hamrock
Attorney, Agent, or Firm—R. B. Ingruham

[57] ABSTRACT

Very desirable polyfunctional lithium containing polymerization initiators are prepared by reacting an adduct of an organo lithium compound and styrene with an organic compound containing at least two 1,1-diphenylethylene groups in the proportion of about two moles of the adduct to one mole of the organic compound. A difunctional lithium initiator is prepared thereby. The difunctional initiator may be reacted with styrene and subsequently an additional quantity of the diphenylethylene compound which in turn is reacted with the styrene-organo lithium adduct to form a trifunctional initiator. The process can be repeated to obtain an initiator having any desired degree of lithium functionality. Such initiators can be prepared in the absence of polar solvents and are very desirable for the polymerization of dienes such as butadiene to a desirable 1,4 configuration and preparation of block copolymers.

9 Claims, No Drawings

POLYFUNCTIONAL LITHIUM CONTAINING INITIATOR

In the polymerization of 1,3-butadiene and isoprene, for many applications, it is highly desirable to polymerize the monomer in such a manner that the amount of 1,4 addition in the polydiene chains is maximized. Desirable initiators of the polymerization are often polyfunctional lithium compounds, that is, compounds having two or more lithium atoms as the polymerization initiating sites and are desirable in the preparation of block copolymers and diene polymers having functional end groups. Many of these multifunctional compounds, from a practical standpoint, fail to provide all that is desired in a polymerization initiator for vinyl group containing compounds such as 1,3-butadiene, isoprene and the like. Oftentimes, traces of polar compounds such as ethers are present. Polar compounds in general tend to increase the amount of 1,2 addition during the polymerization of butadiene or isoprene. Usually it is very desirable to polymerize the diene in a hydrocarbon solvent. For uniformity of the product and maximum control, as well as ease of handling, it is desirable that an initiator be soluble or readily made soluble in the polymerization syste rather than merely dispersible as a particulate material. Multifunctional lithium containing initiators are well known in the art as is the use of such initiators in the polymerization of olefinically unsaturated hydrocarbon monomers. Such polymers and initiators are disclosed in the following U.S. Pat. Nos. 3,660,563; 3,663,634; 3,668,263; 3,684,780; 3,725,368; 3,734,973; 3,776,893; 3,776,964; 3,784,637; 3,787,510, 3,842,145; and 3,954,894, the teachings of which are herewith incorporated by reference thereto. It is known that very desirable lithium initiators can be prepared by the addition of an organo lithium compound to a compound containing two 1,1-diphenylethylene groups.

It would be desirable if there were available an improved polyfunctional lithium containing compound suitable for initiation of polymerization in a hydrocarbon medium.

It would also be desirable if an initiator would be available which would promote polymerization of a 1,3-diene to give a high degree of 1,4 addition.

It would also be desirable if such an initiator were soluble in polymerization initiation quantities in a hydrocarbon medium.

These benefits and other advantages in accordance with the present invention are achieved in a polyfunctional lithium containing polymerization initiating composition containing at least two active lithium atoms, the composition having the formula:

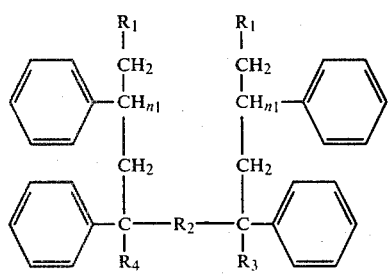

wherein $R_1$ is selected from the group consisting of alkyl, cycloalkyl, and aromatic radicals containing from 1 to 20 carbon atoms, and preferably secondary butyl, $R_2$ is a divalent organic radical having at least 6 carbon atoms, $R_2$ having at least one aromatic ring and the aromatic ring or rings being directly attached to the carbon atoms which are attached to $R_3$ and $R_4$ respectively, with the further limitation $R_2$ contains carbon and hydrocarbon, and optionally oxygen, and/or sulfur, oxygen and sulfur when present are present only in a configuration of a diphenyl oxide or diphenyl sulfide. Preferably $R_2$ contains 6 to 12 carbon atoms and more preferably is 1,4-phenylene

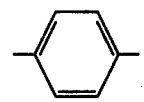

4,4'-biphenylene

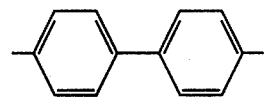

or 4,4'-oxybisphenylene

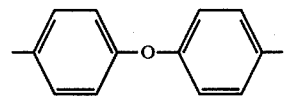

$R_3$ and $R_4$ are individually selected from the group consisting of

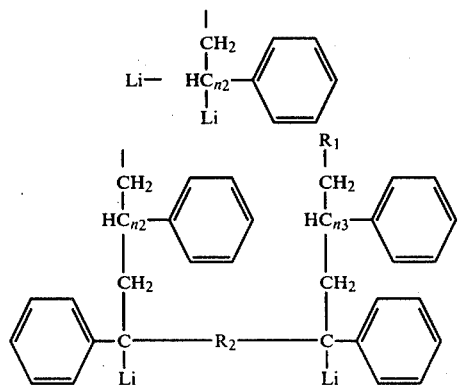

and mixtures thereof, $n_1$, $n_2$ and $n_3$ have average values of 1 or greater. Preferably $n_1$, $n_2$ and $n_3$ have average values of from about 2 to 50 inclusive.

Also contemplated within the scope of the present invention is a solution particularly suited for the initiation of polymerizing of vinyl group containing compounds which are polymerizable in the presence of a lithium containing catalyst, particularly vinyl hydrocarbon compounds, the solution comprising a major portion of a solvent selected from the group consisting of liquid aliphatic, cycloaliphatic and aromatic hydrocarbons and mixtures thereof and a minor proportion of a multifunctional lithium containing polymerization initiating compound of the Formula I.

Also contemplated within the scope of the present invention is a method for the polymerization of vinyl compounds containing at least one vinyl group and particularly vinyl hydrocarbon compounds which are polymerizable in the presence of a lithium containing catalyst, the steps of the method comprising providing at least one compound of Formula I subsequently contacting the resultant solution with at least one lithium polymerizable monomer to cause the polymerization of the monomer to a corresponding polymer.

The simplest embodiment of the present invention is prepared by the reaction of one mole of styrene with one mole of an organo lithium compound, for example, secondary butyl lithium to provide the adduct shown in Formula II:

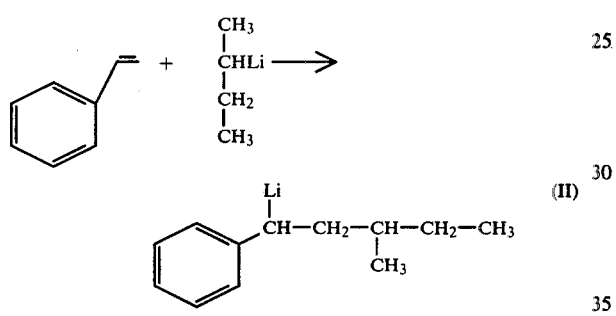

(II)

Two moles of the adduct of Formula II are then reacted with 1,4-bis(1-phenylethenyl)benzene III

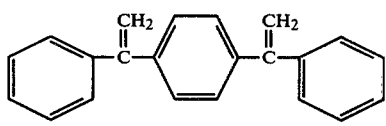

(III)

to provide a difunctional compound of Formula IV:

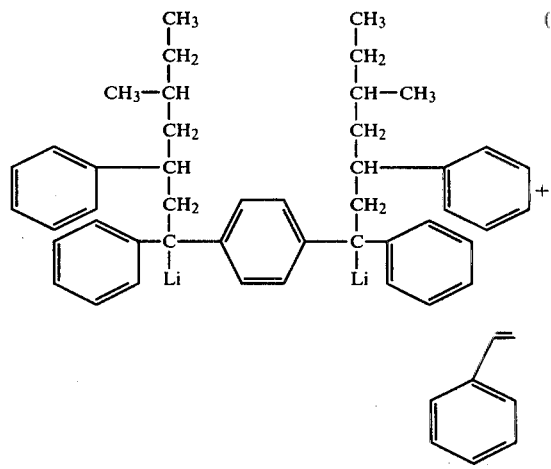

(IV)

The compound of Formula IV is difunctional with respect to lithium and is readily soluble in the usual solvents such as aliphatic, cycloaliphatic and aromatic hydrocarbons employed in lithium initiated polymerizations. If one desires a trifunctional initiator, the compound of Formula IV is reacted with one mole of styrene to provide the compound of Formula V:

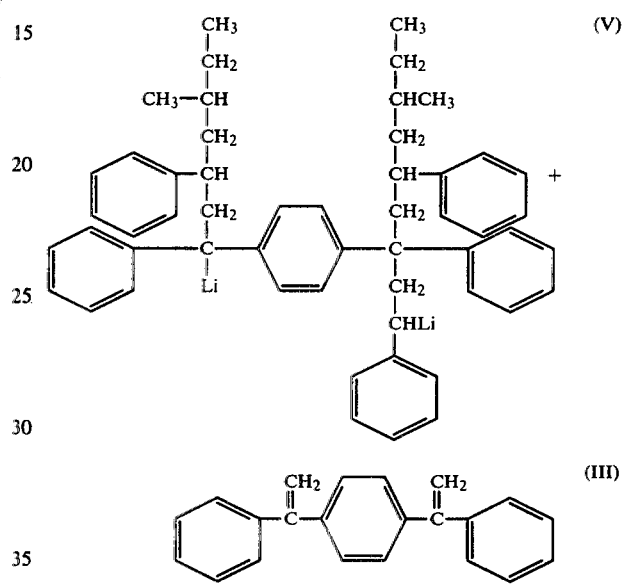

The compound of Formula V is in turn reacted with one mole of the compound of Formula III to provide a compound of Formula VI:

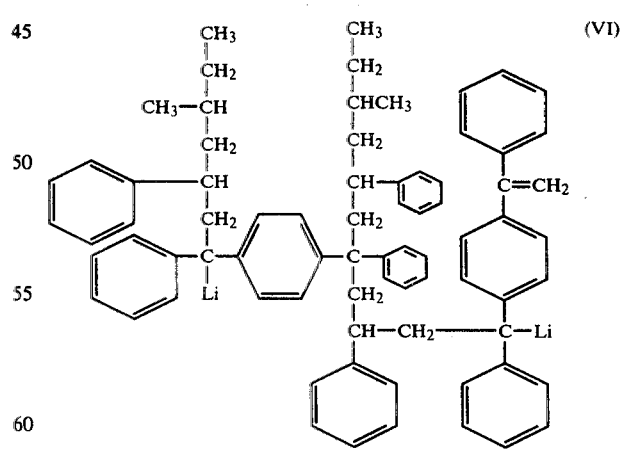

The compound of Formula VI is then reacted with one mole of the compound of Formula II, thus providing an organic soluble trifunctional initiator of Formula VII:

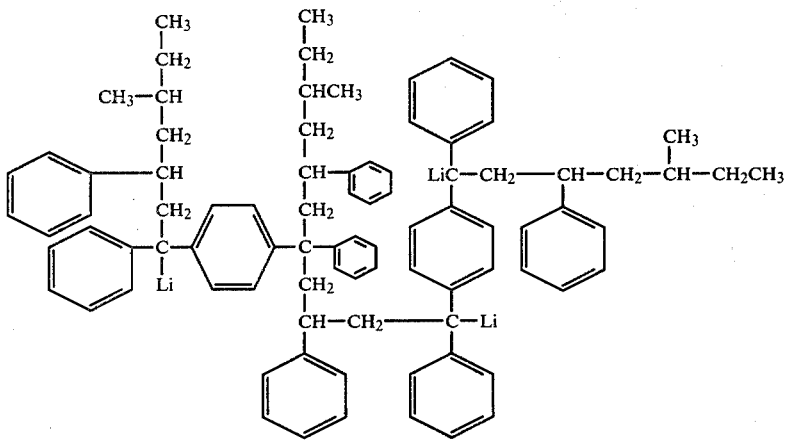

(VII)

thereby providing a trifunctional initiator. Any desired degree of functionality can be obtained by stepwise synthesis as hereinbefore set forth.

Compound VII is an excellent polymerization initiator for the preparation of branched polymers having three arms. If a tetrafunctional initiator is desired, compound (VII) is reacted with an additional mole of styrene, then a mole of compound (III) followed by an additional mole of compound of Formula II.

The hereinbefore described embodiment of the invention represents ideal equimolar reactions. In practice some deviation from the ideal reaction usually occurs. For example, in the preparation of the adduct of Formula II from styrene and secondary butyllithium, the formation of a small amount of a compound having the following formula:

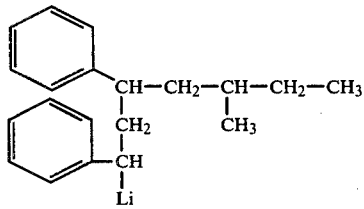

is inevitable and some small amounts of secondary butyllithium will remain unreacted when the reactants are present in exactly equimolar proportions. However, such by-products do not alter the functionality or the solubility of the desired lithium initiator. Therefore, initiators of the present invention when prepared employing coventional chemical practices is a mixture of compounds represented by Formula I with $n_1$ representing the average value of the composition mixture.

Compounds in accordance with the present invention are readily prepared from compounds of the type hereinbefore disclosed and are readily synthesized by condensing an aromatic acid chloride with an aromatic compound such as benzene, biphenyl, diphenyl ether and the like in the presence of a Freidel-Crafts catalyst such as aluminum trichloride to form a diketone, the diketone having the ketone groups separated by at least one aromatic ring. The diketone compound is then subjected to a Wittig reaction which transforms the ketone groups into 1,1-vinylidene groups. The divinylidene compound is then contacted with a 1:1 to 50:1 adduct of styrene and an organolithium compound such as compound II. The adduct adds across the double bonds to provide a dilithium compound generally equivalent to Formula IV, the resulting dilithium compound is then optionally reacted with one or more moles of styrene, to provide a second adduct generally equivalent to Formula V. The second adduct is then reacted with a divinylidene compound generally equivalent to Formula VI and an additional mole of an adduct of the general nature of Formula II to provide a trifunctional adduct generally equivalent to Formula VII.

The invention is further illustrated but not limited by the following examples.

EXAMPLE 1

A difunctional lithium compound was prepared in the following manner: a nitrogen purged reaction vessel was charged with 106.4 grams of aluminum trichloride and a solution of 91.94 grams of benzoylchloride dissolved in 200 milliliters of methylene chloride. A solution of 56 grams of diphenyloxide and 20 milliliters of methylene chloride was cooled to about 0° C. and added to the reaction vessel. After a period of two and one-half hours, the ice bath was removed and the vessel warmed to room temperature and held at ambient temperature for about 20 hours. After 20 hours, some of the methylene chloride had evaporated and was replenished. After an additional hour, the reaction mixture was poured over ice. The resultant aqueous mixture was extracted twice with methylene chloride. The water and organic layers were separated and the water layer was discarded. The organic layer was washed twice with a ten weight percent solution of potassium hydroxide in water. The water layer was discarded. The remaining organic layer was evaporated to dryness. The remaining crude product was dissolved in benzene and decolorized with charcoal. An equal volume of methanol was added to the decolorized benzene solution and 56.03 grams of 4,4'-oxydibenzophenone, was obtained in the form of white, crystal platelets. 10.6 Millimoles of normal butyllithium as 0.53 normal solution in benzene was admixed with 4.06 grams of methyltriphenylphosphonium bromide dissolved in 50 milliliters of tetrahydrofuran in a nitrogen-purged glass reaction vessel and the vessel maintained at ambient temperature at about 22° C. for a period of about two hours. A suspension of 2.05 grams of 4,4'-oxydibenzophenone in 30 milliliters of tetrahydrofuran was added to the reaction mixture. The reaction vessel was maintained at room temperature for a period of about sixteen hours. At the end of this period, the tetrahydrofuran was evaporated and the remaining solid dissolved in a 1:1 by volume diethyl ether-water mixture. The ether and water were separated and the ether layer washed with water. Subsequently, the ether layer was evaporated. The crude bis[4-(1-phenylethenyl)phenyl]ether was recrystallized twice from a 1:1 by volume mixture of benzene and ethenol and the solid product washed with normal hexane. In four runs, bis[4-(1-phenylethenyl)phenyl]ether was employed to react with polystyryl lithium of various chain lengths with varying quantities of styrene. The four runs designated A, B, C and D employed the following quantities:

TABLE

| Run | A | B | C | D |
|---|---|---|---|---|
| Benzene | 32 ml | 30 ml | 30 ml | 10 ml |
| Styrene | 2.6 ml | 0.33 ml | 0.14 ml | 0.40 ml |
| Sec-Butyllithium 0.575M in Cyclohexane | 1.15 milli/-moles | 1.15 milli/-moles | 1.15 milli/-moles | 1.31 milli/-moles |
| bis[4-(1-phenyl-ethenyl)phenyl]ether | 0.199 g | 0.199 g | 0.200 g | 0.239 g |

The reactions were carried out in the following manner: The benzene and styrene were placed in a nitrogen-filled flask. The secondary butyl lithium solution was then injected by means of a hypodermic needle through a rubber septum. In each case, the liquid mixture within the flask turned to the typical orange styryl anion color. In runs A, B, C and D, the average number of styrene units in the oligomer was 20, 2.5, 1 and 3, respectively. After thirty minutes, the bis[4-(1-phenylethenyl)-phenyl]-ether dissolved in 20 milliliters of benzene was injected into the flasks containing mixtures for runs A, B and C while in run D the bis[4-(1-phenylethenyl)-phenyl]ether was dissolved in 10 milliliters of benzene and then injected. The color changed from orange to red and subsequently to a very deep red. The reaction for A, B and C was carried out at room temperature and after 24 hours showed no sign of precipitate. Run D had a reaction time of 105 minutes and showed no precipitate. In Run A, aliquot amounts of samples were withdrawn periodically, quenched with glacial acetic acid and analyzed to gel permeation chromatography. The results indicated that the reaction between the styryl anion and the compound bis[4-(1-phenylethenyl)-phenyl]ether was essentially complete within two hours of the addition of the bis[4-(1-phenylethenyl)-phenyl]ether.

At the end of 24 hours, the reaction mixture of A, 24 milliliters, was admixed with 5 milliliters of isoprene. The solution became orange and after 30 minutes at 60° C. became viscous. A half milliliter of tetrahydrofuran and 0.3 of a milliliter of a solution of one half milliliter of silicon tetrachloride in 9.5 milliliters of benzene was added. A visible gel formed. The gel was isolated by dilution with a 1:1 mixture of benzene and methanol, the gel amounted to about 70 percent of the total mixture. Run C was similarly treated and the gel formed was 78 percent.

The reaction mixture of Run B was employed in the following manner: a nitrogen-filled reaction flask was charged with 450 milliliters of benzene and from about 30 to 35 grams of butadiene. The impurities in the benzene-butadiene mixture were removed by the addition of 0.6 milliliter of a 0.525 N n-butyl lithium in benzene solution. The reaction mixture of Run B was added and the mixture maintained at about 55° C. for 80 minutes. The contents of the reaction flask were then cooled to about 35° C. and 17 milliliters of styrene were added with vigorous agitation. One minute after the addition of the styrene, 2 milliliters of tetrahydrofuran were added. One hour after the addition of the styrene, 0.2 milliliter of glacial acetic acid was added. Fifteen minutes after the addition of the glacial acetic acid, the flask was opened. One gram of a commercially available antioxidant sold under the trade designation IONOL was added to the reaction mixture and the polymer precipitated by the addition of methanol. Forty-nine and one-half grams of triblock copolymer were recovered. The molecular weight was determined by gel permeation chromatography. The molecular weight was 170,000. The copolymer is rubbery and retracts rapidly when released after extension. The tensile strength at break was 1360 pounds per square inch. The elongation at break was in excess of 1000 percent.

The reaction mixture of Run D was added to five hundred milliliters of benzene having dissolved therein 40 grams of butadiene in a nitrogen-filled vacuum flask. The impurities in the benzene-butadiene mixture were removed by the addition of 0.45 millimoles of s-butyl lithium in benzene solution. The mixture in the reaction flask was heated by a water bath maintained within the temperature range of about 50° to 60° for a period of about 60 minutes. The reaction mixture was then cooled to 35° C. and 22 milliliters of purified styrene and 2 milliliters of purified tetrahydrofuran were added. Polymerization within the reaction mixture occurred immediately and was permitted to proceed for 50 minutes without heating or cooling. At the end of the 50 minute period, 0.2 milliliter of glacial acetic acid was added to terminate the anions. The recovered polymer contained 33 weight percent styrene and had a molecular weight of about 100,000 molecular weight units as determined by gel permeation chromatography. A portion of the polymer was molded and had a tensile strength at rupture of 2,040 pounds/square inch and the elongation at break was in excess of 1,000 percent.

EXAMPLE 2

A reaction flask was purged with nitrogen and charged with 58.5 grams of aluminum trichloride and 160 milliliters of benzene. A mixture of 40.6 grams of terephthaloyl chloride in 280 milliliters of benzene was added to the reaction flask from a dropping funnel over a period of 50 minutes. The temperature of the reaction mixture was maintained at about 44°–47° C. for a period of about 40 minutes and raised to 68° C. for about one and one-half hours. The reaction vessel and contents were cooled with an ice-water bath and ice-water mixed with the reaction mixture. Methylene chloride was added and the aqueous and organic layers separated. The organic layer was washed three times with aqueous sodium bicarbonate and washed twice with water. The organic layer was dried over anhydrous sodium sulfate. The particulate sodium sulfate separated and the organic solvents removed by evaporation. The resultant crude product remaining after the evaporation was recrystallized from absolute alcohol containing about 0.5 percent benzene. Thirty grams of 1,4-dibenzoylbenzene were obtained which had a melting range of 155°–160° C. The 1,4-dibenzoylbenzene was converted to 1,4-bis-(1-phenylethenyl)benzene employing the process set forth in Example 1 wherein 4,4'-oxydibenzophenone was converted to bis[4-(1-phenylethenyl)-phenyl]ether.

A solution of polystyryl anions averaging approximately 2.5 styrene units/molecule was prepared by admixing in a flask under a nitrogen atmosphere 11 milliliters of benzene containing 1.478 millimoles of secondary butyl lithium with 0.4 milliliter of styrene. The resultant mixture was allowed to stand at room temperature for 30 minutes. The solution of polystyryl anions was admixed with 0.199 gram of 1,4-bis[1-phenylethenyl]benzene dissolved in 18 milliliters of benzene. One hour and 45 minutes reaction time at room temperature was allowed for the formation of the corresponding dilithium adduct. The resultant mixture hereinafter referred to as the "initiator solution" showed no sign of the formation of a precipitate. A reaction flask provided with a rubber septum was charged with 500 milliliters of benzene and 43 grams of butadiene. Trace impurities were inactivated by the addition of 0.37 millimole of secondary butyllithium. The initiator solution was then added. The reaction mixture was heated in a water bath maintained at a temperature within a range of 50° to 60° C. for a period of 65 minutes. The reaction mixture was then cooled to 40° C. and a mixture of 26 milliliters of styrene and 2 milliliters of tetrahydrofuran were added. Polymerization proceeded for 50 additional minutes without heating or cooling of the reaction mixture. At the end of this period of time, 0.2 milliliter of glacial acetic acid was added to terminate existing anions. Sixty-nine grams of polymer were recovered from the reaction mixture. The polymer contained 34 weight percent styrene and had a molecular weight of 95,000. Test specimens of the polymer were compression molded and indicated a tensile strength at rupture of 1630 lb./sq. inch and an ultimate elongation of 1,100 percent.

EXAMPLE 3

A multifunctional lithium initiator was prepared in the following manner. Polystyryl anions are prepared in two nitrogen-filled reaction flasks. The flasks were charged with the following ingredients: 30 milliliters of benzene containing 1.162 millimoles of secondary butyllithium and 0.2 milliliter of styrene. Both flasks were maintained at room temperature for a period of 30 minutes. At the end of the 30-minute period, each of the flasks was charged with 0.48 millimole of 1,4-bis[1-phenylethenyl]benzene dissolved in 15.9 milliliters of benzene. The flasks were allowed to stand at room temperature for one hour and ten minutes. At the end of this period, 0.6 milliliter of styrene was added to the second flask and the flask and reaction mixture were maintained in a temperature range of 41° to 53° C. for 30 minutes. At the end of this period, 0.24 millimole of 1,4-bis[1-phenylethenyl]benzene dissolved in 8 milliliters of benzene was added. The resultant solution was maintained at room temperature for an additional period of one hour. At the end of this time, 9 milliliters of isoprene were added to the first and second flasks and both flasks and contents maintained at a temperature of between 50° and 60° C. for a period of 30 minutes. At the end of this period, 0.25 millimole of 4,4'-bis(-chloromethyl)diphenyl oxide in benzene and one milliliter of tetrahydrofuran were added. After a 3-minute period, an additional 0.1 millimole of 4,4'-bis(chloromethyl)diphenyl oxide in benzene was added again to each of the two solutions. No change was observed within the first flask which contained a dilithium initiated polyisoprene. The contents of the second flask gelled immediately, thereby indicating its trifunctional nature.

EXAMPLE 4

A nitrogen purged reaction flask was charged with 23.4 grams of biphenyl dissolved in 50 milliliters of 1,2-dichloroethane. 85.5 Grams of benzoylchloride and an additional 100 milliliters of 1,2-dichloroethane were added to the flask. The flask and contents were then cooled to about 10° C. and 71.5 grams of aluminum trichloride was added slowly to the mixture with stirring. The solution became dark red in color. Over a period of about four hours, the temperature of the reaction mixture was raised to 85° C. and maintained at that temperature for a period of 17 hours. At the end of 17 hours, the reaction mixture was poured into ice water with agitation. The reaction mixture and ice water were then extracted with about one liter of methylene chloride. The water layer was discarded and the methylene chloride containing the remaining mixture was washed with first, a sodium bicarbonate solution, and then with water. The methylene chloride solution was agitated with anhydrous sodium sulfate for 30 minutes, the mixture filtered and the filtrate evaporated to dryness. The crude product obtained on drying of the organic layer was then washed with methanol and subsequently with a 1 to 1 mixture of benzene and ethanol. The product was recrystallized from benzene.

17.6 Grams of 4,4'-dibenzoyl-1,1'-biphenyl (Compound A) were obtained having a melting range of 217°–218° C. Examination of the product with an infrared spectroscope indicated an absorbance of a

which agreed with that of the absorbance of benzophenone.

Compound A was converted to 4,4'-bis(1-phenylethenyl)-1,1'-biphenyl (Compound B) in the following manner:

10.6 Millimoles of n-butyllithium as a 0.53 Normal solution in benzene was admixed with 4.06 grams of methyltriphenylphosphonium bromide dissolved in 50 milliliters of tetrahydrofuran in a nitrogen-purged glass reaction vessel and the vessel maintained at ambient temperature (about 22° C.) for a period of 2 hours. A suspension of 2.05 grams of Compound A in 30 milliliters of tetrahydrofuran was added to the reaction mixture. The reaction vessel was maintained at room temperature for a period of about 16 hours. At the end of this period, the tetrahydrofuran was evaporated and the remaining solid dissolved in a 1:1 by volume diethyl ether-water mixture. The ether and water were separated and the ether layer washed with water and subsequently the ether was evaporated. The crude product Compound B was recrystallized twice from a 1 to 1 by volume mixture of benzene and ethanol and the solid product obtained washed with n-hexane, the 4,4'-bis(1-phenylethenyl)1,1'-biphenyl (Compound B) had a melting point of 193°–196° C. A nitrogen-purged reaction flask was charged with 11 milliliters of dry benzene, 0.4 milliliter of styrene and 1.45 millimoles of secondary butyllithium. The flask and contents were maintained at ambient temperature for a period of about 30 minutes to thereby provide a solution of polystyryl anions with a degree of polymerization averaging about 2.5. The resulting polystyryl anion solution was admixed with a solution of 1.417 grams of Compound B dissolved in 35 milliliters of benzene. The resultant mixture turned dark red and within a few minutes turned to a deep blue forming a product (Composition C) having the following average structure:

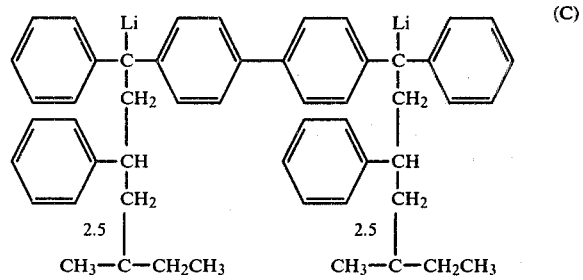

(C)

A period of one hour and forty-five minutes was allowed for completion of the reaction. A solution of 40 grams of butadiene in 450 milliliters of benzene was prepared and impurities removed by treating with 0.35 milliequivalents of secondary butyllithium. The solution of the dilithium composition C and the butadiene in benzene solution were admixed and the reaction vessel placed in a water bath maintained at a temperature of 50° to 60° C. for a period of about 80 minutes. Polymerization of the butadiene was completed at that time. Twenty-three milliliters of styrene and 2 milliliters of tetrahydrofuran were added to the reaction mixture and the water bath removed from the reaction vessel. A period of 40 minutes was allowed for the polymerization of the styrene. At the end of this period, 0.2 milliliter of glacial acetic acid was added to terminate the anions present. The reaction mixture was then poured into methanol to precipitate the polymer. Sixty-three grams of polymer was recovered and on analysis was found to contain about 40 weight percent styrene and have a molecular weight of 85,000 as determined by gel permeation chromatography. A portion of the polymer was compression molded into test specimens. The test specimens were determined to have a tensile strength at break of 1,600 pounds per square inch and an elongation at break in excess of 1,000 percent.

When the procedure of Example 2 is repeated with the substitution of normal butyllithium or phenyllithium for secondary butyllithium similar results are obtained.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A method for the polymerization of vinyl compounds containing at least one vinyl group and particularly vinyl hydrocarbon compounds which are polymerizable in the presence of a lithium containing catalyst, the steps of the method comprising providing a solution of at least one polyfunctional lithium containing polymerization initiating compound containing at least two active lithium atoms, the compound having the formula:

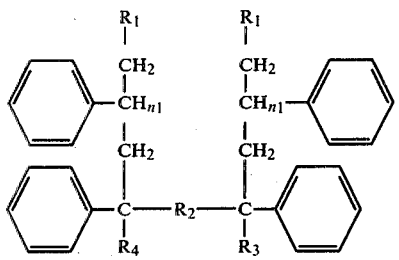

wherein

R$_1$ is selected from the group consisting of alkyl, cycloalkyl, and aromatic radicals containing from 1 to 20 carbon atoms;

R$_2$ is a divalent organic radical having at least 6 carbon atoms, R$_2$ having at least one aromatic ring and the aromatic ring or rings being directly attached to the carbon atoms which are attached to R$_3$ and R$_4$ respectively, with the further limitation R$_2$ contains carbon and hydrocarbon, and optionally oxygen, and/or sulfur, oxygen and sulfur when present are present only in a configuration of a diphenyl oxide or diphenyl sulfide;

and R$_3$ and R$_4$ are individually selected from the group consisting of

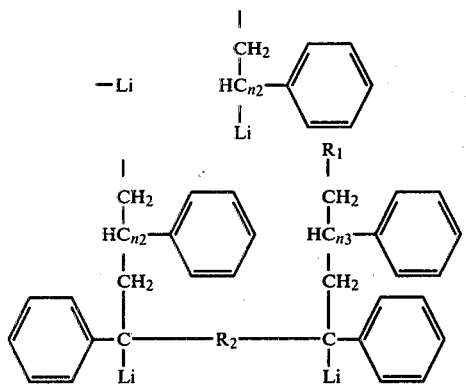

and mixtures thereof, n$_1$, n$_2$ and n$_3$ have average values of 1 or greater, the solution comprising a major portion of a solvent selected from the group consisting of liquid aliphatic, cycloaliphatic, and aromatic hydrocarbons and mixtures thereof and a minor proportion of the polyfunctional lithium containing polymerization initiating compound subsequently contacting the resultant solution with at least one lithium polymerizable monomer to cause the polymerization of the monomer to a corresponding polymer.

2. The method of claim 1 wherein R$_2$ is 1,4-phenylene group.

3. The method of claim 1 wherein R$_2$ is a 4,4'-diphenyloxide group.

4. The method of claim 1 wherein R$_2$ is 4,4'-biphenylene group.

5. The method of claim 1 wherein R$_3$ and R$_4$ are lithium.

6. The method of claim 1 wherein R$_1$ is a 1-methylpropyl radical.

7. The method of claim 1 wherein R$_1$ is 1-methylpropyl radical, R$_2$ is 1,4-phenylene and R$_3$ and R$_4$ are lithium.

8. The method of claim 1 wherein R$_1$ is a 1-methylpropyl radical, R$_2$ is 1,4-diphenyloxide radical and R$_3$ and R$_4$ are lithium.

9. The method of claim 1 wherein R$_1$ is 1-methylpropyl radical, R$_2$ is 4,4'-biphenylene radical and R$_3$ and R$_4$ are lithium.

* * * * *